(12) United States Patent
Hall

(10) Patent No.: US 6,741,056 B1
(45) Date of Patent: May 25, 2004

(54) AIR SAMPLER WITH COMPENSATING PUMP MOTOR SPEED

(75) Inventor: Peter M. Hall, McMurray, PA (US)

(73) Assignee: SKC, Inc., Eighty Four, PA (US)

( * ) Notice: Subject to any disclaimer, the term of this patent is extended or adjusted under 35 U.S.C. 154(b) by 0 days.

(21) Appl. No.: 10/146,369

(22) Filed: May 15, 2002

(51) Int. Cl.[7] .............................................. G05B 11/28
(52) U.S. Cl. ...................... 318/599; 318/459; 318/500; 318/432; 318/434; 318/254; 318/138; 318/439; 417/42; 417/44.1; 417/45; 417/18; 417/22; 73/1.06; 73/1.16; 73/863.02; 73/863.34
(58) Field of Search ................................ 318/599, 811, 318/459, 500, 254, 138, 439, 432, 433, 434, 454; 417/42, 44.1, 45, 18, 22; 73/1.06, 1.16, 836, 863.02, 864.34

(56) References Cited

U.S. PATENT DOCUMENTS

| | | | |
|---|---|---|---|
| 4,241,299 A | * | 12/1980 | Bertone ........................ 318/474 |
| 4,292,574 A | | 9/1981 | Sipin et al. |
| 4,384,825 A | * | 5/1983 | Thomas et al. ............... 417/22 |
| 4,389,903 A | * | 6/1983 | Bertone et al. ........... 73/563.03 |
| 4,527,953 A | | 7/1985 | Baker et al. |
| 4,569,235 A | * | 2/1986 | Conkle et al. ........... 73/863.03 |
| 4,747,315 A | | 5/1988 | Padden |
| 5,019,757 A | * | 5/1991 | Beifus ........................ 318/254 |
| 5,107,713 A | | 4/1992 | Peck et al. |
| 5,263,818 A | * | 11/1993 | Ito et al. ..................... 417/18 |
| 5,313,548 A | | 5/1994 | Arvidson et al. |
| 5,520,517 A | | 5/1996 | Sipin |
| 6,092,992 A | | 7/2000 | Imblum et al. |
| 6,188,947 B1 | | 2/2001 | Zhan |
| 6,273,034 B1 | | 8/2001 | Hawkins et al. |
| 6,343,966 B1 | | 2/2002 | Martin et al. |

* cited by examiner

Primary Examiner—Rina Duda
(74) Attorney, Agent, or Firm—William L. Krayer

(57) ABSTRACT

A constant flow of air through a personal air sampler is provided regardless of changes in the air flow path, by altering the pump speed as a function of the power taken by the pump. The characteristics of the pump are precalibrated to provide a constant used together with the square of the voltage appearing across the motor armature coils (applied voltage minus back Emf), which reflects the power currently used, to adjust the motor speed and thus provide a constant flow of air under changing conditions of resistance.

8 Claims, 1 Drawing Sheet

AIR SAMPLER WITH COMPENSATING PUMP MOTOR SPEED

TECHNICAL FIELD

The air flow produced by a pump motor on a personal air sampler is adjusted automatically to maintain a constant air flow without measuring the actual speed of the pump, and without measuring any pressures, by adjusting the speed of the pump motor according to a calibrated relation of speed to power drawn under loading.

BACKGROUND OF THE INVENTION

Personal air samplers are worn or carried by workers in industrial surroundings and elsewhere to collect particulates, aerosols, microorganisms, chemicals, and other components of the air they breathe. To determine the concentrations of the components in the air, it is necessary to maintain a known flow rate of air over a period of time, preferably a constant flow rate throughout a known time exposure. Factors affecting the ability to provide a constant flow of air in the sampler include the type of pump used, the power supply to the pump, and pressure drops in the air intake, the sampler itself, and the exhaust as the sampler is used. The sampler may have a filter-like particle collector which is expected to cause a resistance to flow as material accumulates on it. A constant flow rate should be maintained in spite of changes in conditions. The present invention is directed to maintaining a constant flow of air through the sampler in spite of resistance to flow caused by random obstructions in the air flow path.

An air sampler as worn or carried by a worker in a factory or other facility typically comprises a small air pump having an air intake, a collector which receives the air from the pump, having an impact surface or a container for collecting aerosols, microorganisms, particulates, and/or chemicals from the air, an exhaust port for the used air, a power supply for the pump, and an electric control for operating the pump. The quantity of collected materials may readily be related to the total volume of air sampled where the air flow is constant and the user accurately records the duration of use.

In the past, complicated circuitry and rechargeable batteries have tended, to make the overall expense of personal samplers inaccessible for some users. A brief review of some of the prior work in the art follows.

Sipin, in U.S. Pat. No. 5,520,517, senses pressure at the outlet of his pump and changes the speed of the pump as dictated by a calibrated relationship of speed to a flow rate over a range of values. Baker et al in U.S. Pat. No. 4,527,953, also monitor actual pressure and in fact maintain a pressure switch operable by pressure drop. Padden, in U.S. Pat. No. 4,747,315, describes a system for adjusting the voltage to, the motor to maintain a desired flow rate.

Peck et al, U.S. Pat. No. 5,101,713, store values representing a relationship between air flow, pump revolutions per minute (RPM), and pulse width modulation (PWM), and then periodically adjust the PWM value to maintain the RPM at a value predetermined to maintain a desired flow rate. See also Arvidson et al U.S. Pat. No. 5,313,548.

In U.S. Pat. No. 4,292,574, Sipin et al maintain a constant motor speed in a system which employs a measurement of back EMF from the motor.

SUMMARY OF THE INVENTION

The present invention provides a constant flow of air through a personal air sampler regardless of changes in the air flow path, by altering the pump speed as a predetermined function of the power drawn under loading.

A typical personal air sampler to which this invention applies has a collector, an air pump, an air pump motor, a portable power supply, and an electrical circuit. As each sampler may vary slightly from unit to unit, or even if not, the sampler is made to include within its electrical circuit a continuous or intermittent measurement of the voltage across (used by) the pump motor. Also, preferably, the circuitry includes a duty cycle control for application of a pulsed voltage. The voltage measurement includes the detection and measurement of back emf generated by the motor between pulses. The change in back emf is directly proportional to the retardation of the pump motor speed due to a back pressure in the air path—accordingly I may use the back emf measurement to increase the voltage to the pump motor in order to increase pump speed to a point known to be capable of providing the desired air flow rate. A correction constant c is therefore built into the microprocessor to permit the circuit to act on the detected back emf.

DETAILED DESCRIPTION OF THE INVENTION

DEFINITIONS

Figure 1:
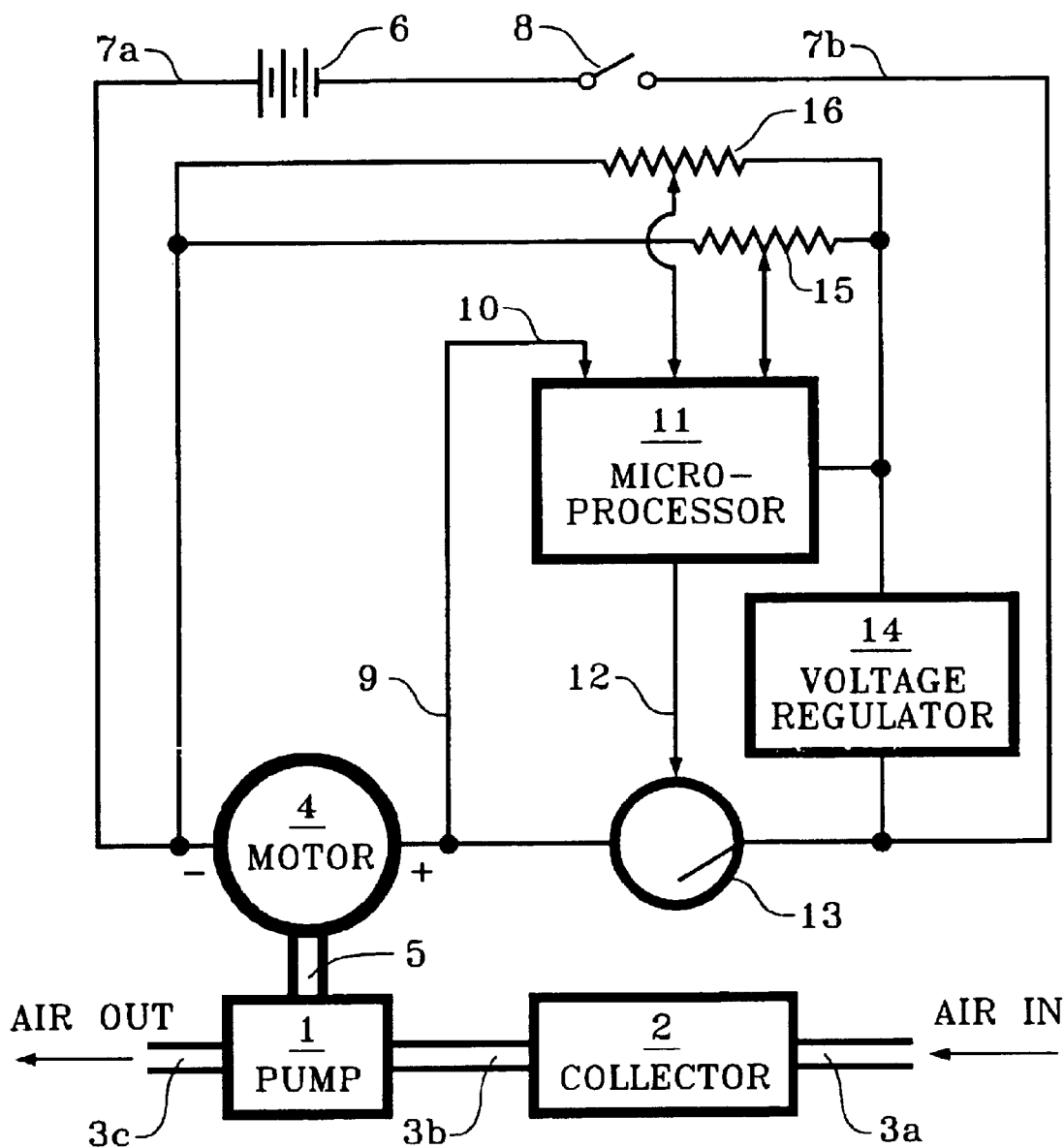
FIG. 1 is a block diagram of the major parts of the personal air sampler of the invention, showing a portion of the circuitry.

Reference pump motor speed: The pump motor speed set for providing an initial air flow through the sampler. It may be optimally determined or set more or less arbitrarily, but the motor speed should be substantially accurate for the desired air flow. In the formula $Sf=S+(S \times C \times ((Va-Vbk) \times D)^2)$, it is represented by S.

Monitoring the power used by the pump motor: Only the voltage is measured; the power is monitored by squaring the factor (applied voltage–Back Emf) and dividing the result by a resistance factor representing the windings of the motor. The resistance factor representing the windings of the motor is a constant for the particular air sampler. Thus the power is a simple function of the applied voltage.

Duty cycle: In a pulse wave modulated system, the ratio of the time length of a pulse to the time interval between pulses. All else being equal an increase in the duty cycle value reflects a proportional increase in power.

Va: Average voltage applied to the motor, as detected by a voltage detector at the intake of the motor and calculated as the average during the "on" time of the duty cycle as applied to the motor. The voltage detector is a simple connection to the circuit upstream of the motor, connected to the microprocessor which converts the voltage from an analog signal to digital.

Back Emf: The reverse electromotive force generated by the motor's turning. It is generated both during and between pulses. Observation and averaging of the Back Emf during the "off" time of the duty cycle in the calculations of the invention permits the use of a simple mathematical calculation to substitute for an actual measurement of pump speed. Average Back Emf is represented as Vbk in the calculation.

C: A constant preferably determined at the time of manufacture and placed in the microprocessor or as an,input to it. The constant is used to modify the Reference pump motor speed as part of the formula $Sf=S+(S\times C\times((Va-Vbk)\times D)^2)$, described elsewhere herein, to provide and provide a new pump motor speed Sf.

C: The duty cycle, specifically the ratio of the duration of a pulse to the duration of the pause before the next pulse. It is independent of current or voltage.

Referring now to FIG. 1, a personal air sampler comprises a pump 1 and a collector 2 for collecting particulates, aerosols, microorganisms, chemicals and the like from air which enters air pathway 3a, drawn by pump 1. The collector 2 may comprise any of many different types of constructions familiar to persons skilled in the art; it may collect specimens by screens, filters, impact or adherence surfaces, gravity, or any other device or construction effective to remove the desired specimens from the air, permitting the air, more or less purged of foreign materials, to continue through the collector 2 to air pathway segment 3b, to pump 1, and out through exhaust segment 3c of the air pathway. Pump 1 is operated by pump motor 4 which turns shaft 5 for the mechanical input to pump 1. When there is no blockage or obstruction in the air pathway 3a–3c, the appropriate rotation speed for shaft 5 can readily be determined for a desired air flow rate through air pathway 3a–3c.

Pump motor 4 is connected to battery or other power source 6 through a basic circuit having circuit segments 7a and 7b, activated by a simple operator's switch 8.

A voltage monitor lead 9 taps the basic circuit at motor 4, and inputs at 10 to microprocessor 11. Voltage regulator 14 assures a stable voltage for microprocessor 11, which incorporates an analog to digital convertor. Microprocessor 11 converts the motor voltage in input 10 to a digital signal and provides a control signal for line 12 to power switch 13, which may be a transistor, FET, or any power control device. In my preferred configuration, the control signal regulates the duty cycle of a pulsed voltage. Sensing the voltage at lead 9 means that the microprocessor will also sense the back Emf during the "down" time of the duty cycle. The back Emf is also averaged for use in the calculation described herein.

An original flow setting is fixed by resistor 16. This is preferably done by the user but could be done at the time of manufacture, and therefore resistor 16 need not be a variable resistor, but could be a fixed resistance, or a signal level could be set (stored) digitally within the microprocessor. The original flow setting is for the voltage necessary in the particular personal air sampler necessary to provide a desired air flow—that is the Reference Pump Motor Speed as defined above.

Also fixed during manufacture is the resistance 15, representing the compensation constant C as defined above. This value could also be incorporated digitally in the microprocessor.

The microprocessor 11 is enabled to execute the formula $Sf=S+(S\times C\times((Va-Vbk)\times D)^2)$ to adjust pump motor speed to a new speed Sf by adjusting the duty cycle applied to the motor through control of power switch 13, where Va is the measured average voltage applied to the motor, S is the original speed set point, D is the duty cycle, and C is a predetermined proportionality constant, and Vbk is the back Emf of the motor, monitored from the same circuit point as the motor.

Summarizing the operation of the personal air sampler, firstly, the unit is calibrated to a desired air flow. That is, a reference pump motor speed is determined to deliver a desired air flow through the collector and the pump. A resistance (16) is set to provide the necessary voltage and therefore the necessary power, to provide the reference pump motor speed, given the constant resistance of the motor windings. The unit is also calibrated to determine a resistance (15) to be used as a compensation constant (C) in a calculation for adjusting the motor speed to provide a constant air flow in spite of increasing (or possibly decreasing) resistance within the air passage 3a–3c. The circuit is designed to read the motor voltage (lead 9) and generate a control signal for power input to the motor (13). This signal is used to regulate either voltage or duty cycle or both. The microprocessor calculates a new motor speed Sf according to the formula $Sf=S+(S\times C\times((Va-Vbk)\times D)^2)$, where the inputs are as defined above. The new speed Sf is proportional to the new power input at a power switch (13), regulated by the microprocessor (11).

Thus, my invention includes a method of maintaining a substantially constant air flow in a personal air sampler having a collector, an air pump, a pump motor, and a battery as a power supply, comprising delivering power to the pump motor from the battery in pulses having a duty cycle, measuring back Emf generated by the pump motor, and modifying the duty cycle as a function of the back Emf to control pump motor speed as a function of a precalibrated constant. My invention also includes a personal air sampler comprising a collector, an air pump, an air pump motor, a portable power supply, and an electrical circuit, the electrical circuit comprising a voltage detector for voltage applied to the motor, the voltage detector being capable of measuring back emf, and a microprocessor for executing the formula $Sf=S+(S\times C\times((Va-Vbk)\times D)^2)$ to adjust pump motors speed to a new speed Sf by adjusting the voltage applied to the motor, where Va is the measured average voltage applied to the motor, S is the original speed set point, D is the duty cycle, and C is a proportionality constant which is predetermined for the personal air sampler, Vbk is the back Emf of the motor. In another aspect, my invention includes a method of controlling pump motor speed to provide a desired air flow rate in a personal air sampler having a pump motor and an air passage, comprising initially calibrating the sampler to determine a multiplier C for the voltage needed to provide a range of pump motor speeds as a linear function of a reference pump motor speed for providing the desired air flow rate when the air passage is substantially unobstructed, continuously or intermittently estimating the change in power used by the pump motor, and using the multiplier C together with the voltage used by the pump motor to adjust there voltage applied to the pump motor to maintain the desired air flow rate when there is resistance to flow in the air passage.

It is not essential in my invention that the motor be run by a pulsed power supply. Rather, in an analog system, for example, Vbk could be determined by measuring the motor rpm and relating that to back Emf by multiplying by a constant representing the relationship between the back Emf and the motor speed. Va could in this case be a variable DC voltage in the formula $Sf=S+(S\times C\times((Va-Vbk)\times D)^2)$, and D would be 1.

What is claimed is:

1. Method of maintaining a substantially constant air flow in a personal air sampler having a collector, an air pump, a pump motor, and a battery as a power supply, comprising delivering power to said pump motor from said battery in pulses having a duty cycle, measuring back Emf generated by said pump motor, and modifying said duty cycle as a function of said back Emf to control pump motor speed as a function of a precalibrated constant, whereby a substantially constant air flow is maintained in said personal air sampler.

2. Method of claim 1 wherein said precalibrated constant is utilized as C in the formula $Sf=S+(S\times C\times((Va-Vbk)\times D)^2)$ to adjust pump motor speed to a new speed Sf by adjusting the voltage applied to said motor, where Va is the measured average voltage applied to said motor, S is the original speed set point, D is the duty cycle, C is a proportionality constant which is predetermined for said personal air sampler, and Vbk is the back Emf of the motor.

3. A personal air sampler comprising a collector, an air pump, an air pump motor, a portable power supply, and an electrical circuit, said electrical circuit comprising a voltage detector for voltage applied to said motor, said voltage detector capable of measuring back emf, and a microprocessor for executing the formula $Sf=S+(S\times C\times((Va-Vbk)\times D)^2)$ to adjust pump motor speed to a new speed Sf by adjusting the voltage applied to said motor, where Va is the measured average voltage applied to said motor, S is the original speed set point, D is the duty cycle, and C is a proportionality constant which is predetermined for said personal air sampler, Vbk is the back Emf of said motor.

4. Personal air sampler of claim 3 wherein said back ernf is monitored from the same circuit point as said motor voltage.

5. Method of controlling pump motor speed to provide a desired air flow rate in a personal air sampler having a pump motor and an air passage, comprising initially calibrating said sampler to determine a multiplier C for the voltage needed to provide a range of pump motor speeds as a linear function of a reference pump motor speed for providing said desired air flow rate when said air passage is substantially unobstructed, continuously or intermittently estimating the change in power used by said pump motor, and using the multiplier C together with the power used by said pump motor to adjust the voltage applied to said pump motor to maintain said desired air flow rate when there is resistance to flow in said air passage.

6. Method of claim 5 wherein said estimate of change in power is made by application of the formula $Sf=S+(S\times C\times((Va-Vbk)\times D)^2)$ where Sf is a new speed, Va is the measured average voltage applied to said motor, S is the original speed set point, D is the duty cycle, C is a proportionality constant which is predetermined for said personal air sampler, and Vbk is the back Emf of said motor.

7. Method of claim 5 wherein said estimating of change in power and said adjustment of voltage are performed by a microprocessor including an analog to digital converter.

8. Method of claim 5 wherein said continuously or intermittently estimating change in power is conducted by continuously or intermittently measuring pump motor speed and estimating said change in power as a function of said pump motor speed.

* * * * *